(12) United States Patent
Stefański et al.

(10) Patent No.: US 10,065,935 B2
(45) Date of Patent: Sep. 4, 2018

(54) DERIVATIVES OF (Z)-1,2-DIPHENYLETHENE

(71) Applicant: UNIWERSYTET MEDYCZNY IM. KAROLA MARCINKOWSKIEGO, Poznań (PL)

(72) Inventors: Tomasz Stefański, Gniezno (PL); Jakub Różański, Poznań (PL); Renata Mikstacka, Poznań (PL); Stanislaw Sobiak, Poznań (PL)

(73) Assignee: Uniwersytet Medyczny IM. Karola Marcinkowskiego (PL)

( * ) Notice: Subject to any disclaimer, the term of this patent is extended or adjusted under 35 U.S.C. 154(b) by 339 days.

(21) Appl. No.: 14/389,281

(22) PCT Filed: Mar. 28, 2013

(86) PCT No.: PCT/PL2013/000042
§ 371 (c)(1),
(2) Date: Sep. 29, 2014

(87) PCT Pub. No.: WO2013/147629
PCT Pub. Date: Oct. 3, 2013

(65) Prior Publication Data
US 2015/0065727 A1 Mar. 5, 2015

(30) Foreign Application Priority Data
Mar. 29, 2012 (PL) .......................... 398659

(51) Int. Cl.
| | | |
|---|---|---|
| *C07D 263/32* | (2006.01) | |
| *C07D 233/64* | (2006.01) | |
| *C07C 323/62* | (2006.01) | |
| *C07C 333/04* | (2006.01) | |
| *C07C 323/18* | (2006.01) | |

(52) U.S. Cl.
CPC .......... *C07D 263/32* (2013.01); *C07C 323/18* (2013.01); *C07C 323/62* (2013.01); *C07C 333/04* (2013.01); *C07D 233/64* (2013.01)

(58) Field of Classification Search
None
See application file for complete search history.

(56) References Cited

U.S. PATENT DOCUMENTS

2006/0160773 A1   7/2006   Giannini et al.

FOREIGN PATENT DOCUMENTS

WO         02/50007 A2        6/2002

OTHER PUBLICATIONS

Bernhard Biersack, Natural product derived cytostatics with improved tumor selectivity and potential to overcome drug resistance, Dissertation, <http://www.memd.de/?recid=405731> (2010).*
International Search Report for International Application No. PCT/PL2013/000042 dated Jul. 29, 2013.

* cited by examiner

*Primary Examiner* — Alicia L Otton
(74) *Attorney, Agent, or Firm* — Katten Muchin Rosenman LLP

(57) ABSTRACT

The present invention relates to the new chemical compounds containing (Z)-1,2-diphenylethene moiety in the structures, particularly the new derivatives of cis-stilbene, the new derivatives of 4,5-diphenyl-1,3-oxazole, the new derivatives of 1-methyl-4,5-diphenyl-1H-imidazole and pharmaceutically acceptable salts thereof. The invention relates also to the application of aforementioned compounds as a microtubule-interfering agents (MIAs). The new derivatives, because of their potential antimitotic and antiangiogenic activity, can be used as ingredients in the preparations used in the treatment of cancer.

8 Claims, 1 Drawing Sheet formula 1 formula 2 formula 3

DERIVATIVES OF (Z)-1,2-DIPHENYLETHENE

THE FIELD OF THE INVENTION

The present invention relates to the new chemical compounds containing (Z)-1,2-diphenylethene moiety in the structures, particularly the new derivatives of cis-stilbene, the new derivatives of 4,5-diphenyl-1,3-oxazole, the new derivatives of 1-methyl-4,5-diphenyl-1H-imidazole and pharmaceutically acceptable salts thereof. The invention relates also to the application of aforementioned compounds as a microtubule-interfering agents (MIAs).

BACKGROUND OF THE INVENTION

Figure 1:
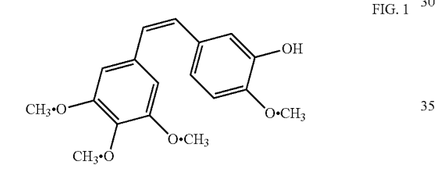
FIG. 1—presents the general formulas of the new derivatives of cis-stilbene (formula 1), the new derivatives of 4,5-diphenyl-1,3-oxazole (formula 2) and the new derivatives of 1-methyl-4,5-diphenyl-1H-imidazole (formula 3).

The plant polyphenols, in particular derivatives of cis-stilbene, are promising group of anti-carcinogenic agents. Combretastatin A-4 (CA-4, 3'-hydroxy-3,4,4',5-tetramethoxy-cis-stilbene) is the leading substance for compounds of such structure and the best-known tubulin polymerization inhibitor (FIG. 1). One of the CA-4 pro-drug form—disodium phosphate (Zybrestat™)—is currently in phase 3 of clinical trials for the treatment of very aggressive and drug resistant form of anaplastic thyroid cancer (Siemann, D. W.; Chaplin, D. J.; Walicke, P. A. *Expert Opin. Inv. Drugs* 2009, 18, 189-197).

FIG. 1

Antimitotic activity of CA-4 is the result of its interaction with tubulin—protein forming microtubules in the cell nucleus—considered as the best molecular target for anticancer chemotherapeutics. Noteworthy, cis-stilbene derivatives accelerate depolymerization of tubulin inhibiting the formation of microtubules therefore, while the trans-stilbenes influence in the process of tubulin polymerization. Compounds of both groups, known as microtubule-interfering agents (MIAs), have affinity to the different binding sites on the tubulin surface, which affects the balance between two processes inside cancer cells, polymerization and depolymerization of microtubules (Singh, P.; Rathinasamy, K.; Mohan, R.; Panda, D. *IUBMB Life* 2008, 60, 368-375). It leads to arresting the cell cycle in the G2/M phase, which is accompanied by the activation of apoptotic signalling pathways (Li, H.; Wu, W. K. K.; Zheng, A.; Che, C. T.; Yu, L. et al. *Biochem. Pharmacol.* 2009, 78, 1224-1232). In addition, combretastatin shows strong antiangiogenic activity by selectively inhibition of the new blood vessels formation in cancer tissue (Thorpe, E. P. *Clin. Cancer Res.* 2004, 10, 415-4270. Tozer, G. M.; Kanthou, C.; Parkins, C. S.; Hill, S. A. *Int. J. Exp. Pathol.* 2001, 83, 21-38).

Figure 2:
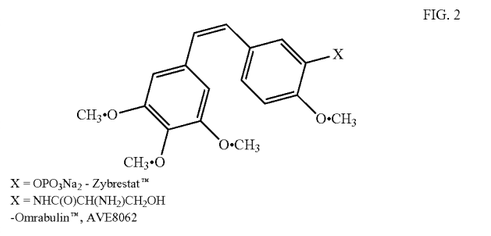

In recent years, a number of structural modifications of CA-4 were performed allowing for identification of substituents affecting the activity of different analogues. It has been found that the presence of methoxy radicals at 3-, 4-, 5-positions in phenyl ring is crucial in the context of pharmacological effect (Tron, G. C.; Pirali, T.; Sorba, G.; Pagliai, F.; Busacca, S.; Genazzani, A. *J. Med. Chem.* 2006, 49, 3033-3044). On the other hand, modification involving ethylene chain stiffening with an oxazole or N-methylimidazole ring proved to be effective in preventing the conversion from cis to the trans isomer, which increased the cytotoxic effect against cancer cells. At the same time efforts aimed at improving the bioavailability of CA-4 derivatives made it possible to obtain the corresponding prodrugs—the aforementioned Zybrestat™ (Tron, G. C.; Pirali, T.; Sorba, G.; Pagliai, F.; Busacca, S.; Genazzani, A. *J. Med. Chem.* 2006, 49, 3033-3044) and serine derivative—Omrabulin™ or AVE8062 (Delmonte, A., Sessa, C.; *Expert Opin. Inv. Drugs* 2009, 18, 1541-1548). These compounds (FIG. 2) are subject to biotransformation—dephosphorylation and deacetylation respectively—to biologically active molecules.

FIG. 2

DESCRIPTION OF THE INVENTION

In its first aspect, the invention provides the new chemical compounds containing (Z)-1,2-diphenylethene moiety in the structures particularly the new derivatives of cis-stilbene, the new derivatives of 4,5-diphenyl-1,3-oxazole, the new derivatives of 1-methyl-4,5-diphenyl-1H-imidazole and pharmaceutically acceptable salts thereof.

According to the first aspect, the present invention relates to the new cis-stilbene derivatives of general formula 1, (1)

wherein:
$R^1$=SCH$_3$, $R^2$=H, $R^3$=H, $R^4$=H, $R^5$=OCH$_3$, $R^6$=OCH$_3$, $R^7$=OCH$_3$, $R^8$=H, $R^9$=COOH (1); $R^1$=SCH$_3$, $R^2$=H, $R^3$=H, $R^4$=H, $R^5$=OCH$_3$, $R^6$=OCH$_3$, $R^7$=OCH$_3$, $R^8$=H, $R^9$=H (2); $R^1$=OC(S)N(CH$_3$)$_2$, $R^2$=OCH$_3$, $R^3$=H, $R^4$=H, $R^5$=OCH$_3$, $R^6$=OCH$_3$, $R^7$=OCH$_3$, $R^8$=H, $R^9$=COOH (3); $R^1$=SC(O)N(CH$_3$)$_2$, $R^2$=OCH$_3$, $R^3$=H, $R^4$=H, $R^5$=OCH$_3$, $R^6$=OCH$_3$, $R^7$=OCH$_3$, $R^8$=H, $R^9$=COOH (4); $R^1$=SCH$_3$, $R^2$=OCH$_3$, $R^3$=H, $R^4$=H, $R^5$=OCH$_3$, $R^6$=OCH$_3$, $R^7$=OCH$_3$, $R^8$=H, $R^9$=COOH (5); $R^1$=OC(S)N(CH$_3$)$_2$, $R^2$=OCH$_3$, $R^3$=H, $R^4$=H, $R^5$=OCH$_3$, $R^6$=OCH$_3$, $R^7$=OCH$_3$, $R^8$=H, $R^9$=H (6); $R^1$=SC(O)N(CH$_3$)$_2$, $R^2$=OCH$_3$, $R^3$=H, $R^4$=H, $R^5$=OCH$_3$, $R^6$=OCH$_3$, $R^7$=OCH$_3$, $R^8$=H, $R^9$=H (7); $R^1$=SCH$_3$, $R^2$=OCH$_3$, $R^3$=H, $R^4$=H, $R^5$=OCH$_3$, $R^6$=OCH$_3$, $R^7$=OCH$_3$, $R^8$=H, $R^9$=H (8); $R^1$=H, $R^2$=OC(S)N(CH$_3$)$_2$, $R^3$=OCH$_3$, $R^4$=H, $R^5$=OCH$_3$, $R^6$=OCH$_3$, $R^7$=OCH$_3$, $R^8$=H, $R^9$=COOH (9); $R^1$=H, $R^2$=SC(O)N(CH$_3$)$_2$, $R^3$=OCH$_3$, $R^4$=H, $R^5$=OCH$_3$, $R^6$=OCH$_3$, $R^7$=OCH$_3$, $R^8$=H, $R^9$=COOH (10); Fe=H, $R^2$=SCH$_3$, $R^3$=OCH$_3$, $R^4$=H, $R^5$=OCH$_3$, $R^6$=OCH$_3$, $R^7$=OCH$_3$, $R^8$=H, $R^9$=COOH (11); $R^1$=H, $R^2$=SCH$_3$, $R^3$=OCH$_3$, $R^4$=H, $R^5$=OCH$_3$, $R^6$=OCH$_3$, $R^7$=OCH$_3$, $R^8$=H, $R^9$=H (12); $R^1$=H, $R^2$=OCH$_3$, $R^3$=OC(S)N(CH$_3$)$_2$, $R^4$=H, $R^5$=OCH$_3$, $R^6$=OCH$_3$, $R^7$=OCH$_3$, $R^8$=H, $R^9$=COOH (13); $R^1$=H, $R^2$=OCH$_3$, $R^3$=SC(O)N(CH$_3$)$_2$, $R^4$=H, $R^5$=OCH$_3$, $R^6$=OCH$_3$, $R^7$=OCH$_3$, $R^8$=H, $R^9$=COOH (14); $R^1$=H, $R^2$=OCH$_3$, $R^3$=SCH$_3$, $R^4$=H, $R^5$=OCH$_3$, $R^6$=OCH$_3$, $R^7$=OCH$_3$, $R^8$=H, $R^9$=COOH (15); $R^1$=H, $R^2$=OCH$_3$, $R^3$=OC(S)N(CH$_3$)$_2$, $R^4$=H, $R^5$=OCH$_3$, $R^6$=OCH$_3$, $R^7$=OCH$_3$, $R^8$=H, $R^9$=H (16); $R^1$=H, $R^2$=OCH$_3$, $R^3$=SC(O)N(CH$_3$)$_2$, $R^4$=H, $R^5$=OCH$_3$, $R^6$=OCH$_3$, $R^7$=OCH$_3$, $R^8$=H, $R^9$=H (17); $R^1$=H, $R^2$=OCH$_3$, $R^3$=SCH$_3$, $R^4$=H, $R^5$=OCH$_3$, $R^6$=OCH$_3$, $R^7$=OCH$_3$, $R^8$=H, $R^9$=H (18); $R^1$=H, $R^2$=OCH$_3$, $R^3$=OC(S)N(CH$_3$)$_2$, $R^4$=OCH$_3$, $R^5$=H, $R^6$=H, $R^7$=H, $R^8$=OCH$_3$, $R^9$=COOH (19); $R^1$=H, $R^2$=OCH$_3$, $R^3$=SC(O)N(CH$_3$)$_2$, $R^4$=OCH$_3$, $R^5$=H, $R^6$=H, $R^7$=H, $R^8$=OCH$_3$, $R^9$=COOH (20); $R^1$=H, $R^2$=OCH$_3$, $R^3$=SCH$_3$, $R^4$=OCH$_3$, $R^5$=H, $R^6$=H, $R^7$=H, $R^8$=OCH$_3$, $R^9$=COOH (21); $R^1$=H, $R^2$=OCH$_3$, $R^3$=OC(S)N(CH$_3$)$_2$, $R^4$=OCH$_3$, $R^5$=H, $R^6$=H, $R^7$=H, $R^8$=OCH$_3$, $R^9$=H (22); $R^1$=H, $R^2$=OCH$_3$, $R^3$=SC(O)N(CH$_3$)$_2$, $R^4$=OCH$_3$, $R^5$=H, $R^6$=H, $R^7$=H, $R^8$=OCH$_3$, $R^9$=H (23); $R^1$=H, $R^2$=OCH$_3$, $R^3$=SCH$_3$, $R^4$=OCH$_3$, $R^5$=H, $R^6$=H, $R^7$=H, $R^8$=OCH$_3$, $R^9$=H (24); $R^1$=H, $R^2$=OCH$_3$, $R^3$=OC(S)N(CH$_3$)$_2$, $R^4$=Br, $R^5$=H, $R^6$=H, $R^7$=H, $R^8$=OCH$_3$, $R^9$=COOH (25); $R^1$=H, $R^2$=OCH$_3$, $R^3$=SC(O)N(CH$_3$)$_2$, $R^4$=Br, $R^5$=H, $R^6$=H, $R^7$=H, $R^8$=OCH$_3$, $R^9$=COOH (26); $R^1$=H, $R^2$=OCH$_3$, $R^3$=SCH$_3$, $R^4$=Br, $R^5$=H, $R^6$=H, $R^7$=H, $R^8$=OCH$_3$, $R^9$=COOH (27); $R^1$=H, $R^2$=OCH$_3$, $R^3$=OC(S)N(CH$_3$)$_2$, $R^4$=Br, $R^5$=H, $R^6$=H, $R^7$=H, $R^8$=OCH$_3$, $R^9$=H (28); $R^1$=H, $R^2$=OCH$_3$, $R^3$=SC(O)N(CH$_3$)$_2$, $R^4$=Br, $R^5$=H, $R^6$=H, $R^7$=H, $R^8$=OCH$_3$, $R^9$=H (29); $R^1$=H, $R^2$=OCH$_3$, $R^3$=SCH$_3$, $R^4$=Br, $R^5$=H, $R^6$=H, $R^7$=H, $R^8$=OCH$_3$, $R^9$=H (30); $R^1$=H, $R^2$=Br, $R^3$=OC(S)N(CH$_3$)$_2$, $R^4$=Br, $R^5$=H, $R^6$=H, $R^7$=H, $R^8$=OCH$_3$, $R^9$=COOH (31); $R^1$=H, $R^2$=Br, $R^3$=SC(O)N(CH$_3$)$_2$, $R^4$=Br, $R^5$=H, $R^6$=H, $R^7$=H, $R^8$=OCH$_3$, $R^9$=COOH (32); $R^1$=H, $R^2$=Br, $R^3$=SCH$_3$, $R^4$=Br, $R^5$=H, $R^6$=H, $R^7$=H, $R^8$=OCH$_3$, $R^9$=COOH (33); $R^1$=H, $R^2$=Br, $R^3$=OC(S)N(CH$_3$)$_2$, $R^4$=Br, $R^5$=H, $R^6$=H, $R^7$=H, $R^8$=OCH$_3$, $R^9$=H (34); $R^1$=H, $R^2$=Br, $R^3$=SC(O)N(CH$_3$)$_2$, $R^4$=Br, $R^5$=H, $R^6$=H, $R^7$=H, $R^8$=OCH$_3$, $R^9$=H (35); $R^1$=H, $R^2$=Br, $R^3$=SCH$_3$, $R^4$=Br, $R^5$=H, $R^6$=H, $R^7$=H, $R^8$=OCH$_3$, $R^9$=H (36); $R^1$=H, $R^2$=OCH$_3$, $R^3$=OC(S)N(CH$_3$)$_2$, $R^4$=OCH$_3$, $R^5$=H, $R^6$=H, $R^7$=OCH$_3$, $R^8$=H, $R^9$=COOH (37); $R^1$=H, $R^2$=OCH$_3$, $R^3$=SC(O)N(CH$_3$)$_2$, $R^4$=OCH$_3$, $R^5$=H, $R^6$=H, $R^7$=OCH$_3$, $R^8$=H, $R^9$=COOH (38); $R^1$=H, $R^2$=OCH$_3$, $R^3$=SCH$_3$, $R^4$=OCH$_3$, $R^5$=H, $R^6$=H, $R^7$=OCH$_3$, $R^8$=H, $R^9$=COOH (39); $R^1$=H, $R^2$=OCH$_3$, $R^3$=OC(S)N(CH$_3$)$_2$, $R^4$=OCH$_3$, $R^5$=H, $R^6$=H, $R^7$=OCH$_3$, $R^8$=H, $R^9$=H (40); $R^1$=H, $R^2$=OCH$_3$, $R^3$=SC(O)N(CH$_3$)$_2$, $R^4$=OCH$_3$, $R^5$=H, $R^6$=H, $R^7$=OCH$_3$, $R^8$=H, $R^9$=H (41); $R^1$=H, $R^2$=OCH$_3$, $R^3$=SCH$_3$, $R^4$=OCH$_3$, $R^5$=H, $R^6$=H, $R^7$=OCH$_3$, $R^8$=H, $R^9$=H (42); $R^1$=H, $R^2$=OCH$_3$, $R^3$=OC(S)N(CH$_3$)$_2$, $R^4$=Br, $R^5$=H, $R^6$=H, $R^7$=OCH$_3$, $R^8$=H, $R^9$=COOH (43); $R^1$=H, $R^2$=OCH$_3$, $R^3$=SC(O)N(CH$_3$)$_2$, $R^4$=Br, $R^5$=H, $R^6$=H, $R^7$=OCH$_3$, $R^8$=H, $R^9$=COOH (44); $R^1$=H, $R^2$=OCH$_3$, $R^3$=SCH$_3$, $R^4$=Br, $R^5$=H, $R^6$=H, $R^7$=OCH$_3$, $R^8$=H, $R^9$=COOH (45); $R^1$=H, $R^2$=OCH$_3$, $R^3$=OC(S)N(CH$_3$)$_2$, $R^4$=Br, $R^5$=H, $R^6$=H, $R^7$=OCH$_3$, $R^8$=H, $R^9$=H (46); $R^1$=H, $R^2$=OCH$_3$, $R^3$=SC(O)N(CH$_3$)$_2$, $R^4$=Br, $R^5$=H, $R^6$=H, $R^7$=OCH$_3$, $R^8$=H, $R^9$=H (47); $R^1$=H, $R^2$=OCH$_3$, $R^3$=SCH$_3$, $R^4$=Br, $R^5$=H, $R^6$=H, $R^7$=OCH$_3$, $R^8$=H, $R^9$=H (48); $R^1$=H, $R^2$=Br, $R^3$=OC(S)N(CH$_3$)$_2$, $R^4$=Br, $R^5$=H, $R^6$=H, $R^7$=OCH$_3$, $R^8$=H, $R^9$=COOH (49); $R^1$=H, $R^2$=Br, $R^3$=SC(O)N(CH$_3$)$_2$, $R^4$=Br, $R^5$=H, $R^6$=H, $R^7$=OCH$_3$, $R^8$=H, $R^9$=COOH (50); $R^1$=H, $R^2$=Br, $R^3$=SCH$_3$, $R^4$=Br, $R^5$=H, $R^6$=H, $R^7$=OCH$_3$, $R^8$=H, $R^9$=COOH (51); $R^1$=H, $R^2$=Br, $R^3$=OC(S)N(CH$_3$)$_2$, $R^4$=Br, $R^5$=H, $R^6$=H, $R^7$=OCH$_3$, $R^8$=H, $R^9$=H (52); $R^1$=H, $R^2$=Br, $R^3$=SC(O)N(CH$_3$)$_2$, $R^4$=Br, $R^5$=H, $R^6$=H, $R^7$=OCH$_3$, $R^8$=H, $R^9$=H (53); $R^1$=H, $R^2$=Br, $R^3$=SCH$_3$, $R^4$=Br, $R^5$=H, $R^6$=H, $R^7$=OCH$_3$, $R^8$=H, $R^9$=H (54); $R^1$=H, $R^2$=OCH$_3$, $R^3$=OC(S)N(CH$_3$)$_2$, $R^4$=OCH$_3$, $R^5$=H, $R^6$=OCH$_3$, $R^7$=H, $R^8$=H, $R^9$=COOH (55); =H, $R^2$=OCH$_3$, $R^3$=SC(O)N(CH$_3$)$_2$, $R^4$=OCH$_3$, $R^5$=H, $R^6$=OCH$_3$, $R^7$=H, $R^8$=H, $R^9$=COOH (56); $R^1$=H, $R^2$=OCH$_3$, $R^3$=SCH$_3$, $R^4$=OCH$_3$, $R^5$=H, $R^6$=OCH$_3$, $R^7$=H, $R^8$=H, $R^9$=COOH (57); $R^1$=H, $R^2$=OCH$_3$, $R^3$=OC(S)N(CH$_3$)$_2$, $R^4$=OCH$_3$, $R^5$=H, $R^6$=OCH$_3$, $R^7$=H, $R^8$=H, $R^9$=H (58); $R^1$=H, $R^2$=OCH$_3$, $R^3$=SC(O)N(CH$_3$)$_2$, $R^4$=OCH$_3$, $R^5$=H, $R^6$=OCH$_3$, $R^7$=H, $R^8$=H, $R^9$=H (59); $R^1$=H, $R^2$=OCH$_3$, $R^3$=SCH$_3$, $R^4$=OCH$_3$, $R^5$=H, $R^6$=OCH$_3$, $R^7$=H, $R^8$=H, $R^9$=H (60); $R^1$=H, $R^2$=OCH$_3$, $R^3$=OC(S)N(CH$_3$)$_2$, $R^4$=Br, $R^5$=H, $R^6$=OCH$_3$, $R^7$=H, $R^8$=H, $R^9$=COOH (61); $R^1$=H, $R^2$=OCH$_3$, $R^3$=SC(O)N(CH$_3$)$_2$, $R^4$=Br, $R^5$=H, $R^6$=OCH$_3$, $R^7$=H, $R^8$=H, $R^9$=COOH (62); $R^1$=H, $R^2$=OCH$_3$, $R^3$=SCH$_3$, $R^4$=Br, $R^5$=H, $R^6$=OCH$_3$, $R^7$=H, $R^8$=H, $R^9$=COOH (63); $R^1$=H, $R^2$=OCH$_3$, $R^3$=OC(S)N(CH$_3$)$_2$, $R^4$=Br, $R^5$=H, $R^6$=OCH$_3$, $R^7$=H, $R^8$=H, $R^9$=H (64); $R^1$=H, $R^2$=OCH$_3$, $R^3$=SC(O)N(CH$_3$)$_2$, $R^4$=Br, $R^5$=H, $R^6$=OCH$_3$, $R^7$=H, $R^8$=H, $R^9$=H (65); $R^1$=H, $R^2$=OCH$_3$, $R^3$=SCH$_3$, $R^4$=Br, $R^5$=H, $R^6$=OCH$_3$, $R^7$=H, $R^8$=H, $R^9$=H (66); $R^1$=H, $R^2$=Br, $R^3$=OC(S)N(CH$_3$)$_2$, $R^4$=Br, $R^5$=H, $R^6$=OCH$_3$, $R^7$=H, $R^8$=H, $R^9$=COOH (67); $R^1$=H, $R^2$=Br, $R^3$=SC(O)N(CH$_3$)$_2$, $R^4$=Br, $R^5$=H, $R^6$=OCH$_3$, $R^7$=H, $R^8$=H, $R^9$=COOH (68); $R^1$=H, $R^2$=Br, $R^3$=SCH$_3$, $R^4$=Br, $R^5$=H, $R^6$=OCH$_3$, $R^7$=H, $R^8$=H, $R^9$=COOH (69); $R^1$=H, $R^2$=Br, $R^3$=OC(S)N(CH$_3$)$_2$, $R^4$=Br, $R^5$=H, $R^6$=OCH$_3$, $R^7$=H, $R^8$=H, $R^9$=H (70); $R^1$=H, $R^2$=Br, $R^3$=SC(O)N(CH$_3$)$_2$, $R^4$=Br, $R^5$=H, $R^6$=OCH$_3$, $R^7$=H, $R^8$=H, $R^9$=H (71); $R^1$=H, $R^2$=Br, $R^3$=SCH$_3$, $R^4$=Br, $R^5$=H, $R^6$=OCH$_3$, $R^7$=H, $R^8$=H, $R^9$=H (72); $R^1$=H, $R^2$=OCH$_3$, $R^3$=OCH$_3$, $R^4$=OCH$_3$, $R^5$=H, $R^6$=H, $R^7$=SCH$_3$, $R^8$=H, $R^9$=COOH (73); $R^1$=H, $R^2$=OCH$_3$, $R^3$=OCH$_3$, $R^4$=OCH$_3$, $R^5$=H, $R^6$=H, $R^7$=SCH$_3$, $R^8$=H, $R^9$=H (74); $R^1$=H, $R^2$=OCH$_3$, $R^3$=OH, $R^4$=OCH$_3$, $R^5$=H, $R^6$=H, $R^7$=SCH$_3$, $R^8$=H, $R^9$=COOH (75); $R^1$=H, $R^2$=OCH$_3$, $R^3$=OC(S)N(CH$_3$)$_2$, $R^4$=OCH$_3$, $R^5$=H, $R^6$=H, $R^7$=SCH$_3$, $R^8$=H, $R^9$=COOH (76); $R^1$=H, $R^2$=OCH$_3$, $R^3$=SC(O)N(CH$_3$)$_2$, $R^4$=OCH$_3$, $R^5$=H, $R^6$=H, $R^7$=SCH$_3$, $R^8$=H, $R^9$=COOH (77); $R^1$=H, $R^2$=OCH$_3$, $R^3$=SCH$_3$, $R^4$=OCH$_3$, $R^5$=H, $R^6$=H, $R^7$=SCH$_3$, $R^8$=H, $R^9$=COOH (78); Fe=H, $R^2$=OCH$_3$, $R^3$=OH, $R^4$=OCH$_3$, $R^5$=H, $R^6$=H, $R^7$=SCH$_3$, $R^8$=H, $R^9$=H (79); $R^1$=H, $R^2$=OCH$_3$, $R^3$=OC(S)N(CH$_3$)$_2$, $R^4$=OCH$_3$, $R^5$=H, $R^6$=H, $R^7$=SCH$_3$, $R^8$=H, $R^9$=H (80); $R^1$=H, $R^2$=OCH$_3$, $R^3$=SC(O)N(CH$_3$)$_2$, $R^4$=OCH$_3$, $R^5$=H, $R^6$=H, $R^7$=SCH$_3$, $R^8$=H, $R^9$=H (81); $R^1$=H, $R^2$=OCH$_3$, $R^3$=SCH$_3$, $R^4$=OCH$_3$, $R^5$=H, $R^6$=H, $R^7$=SCH$_3$, $R^8$=H, $R^9$=H (82); $R^1$=H, $R^2$=OCH$_3$, $R^3$=OH, $R^4$=Br, $R^5$=H, $R^6$=H, $R^7$=SCH$_3$, $R^8$=H, $R^9$=COOH (83); $R^1$=H, $R^2$=OCH$_3$, $R^3$=OC(S)N(CH$_3$)$_2$, $R^4$=Br, $R^5$=H, $R^6$=H, $R^7$=SCH$_3$, $R^8$=H, $R^9$=COOH (84); Fe=H, $R^2$=OCH$_3$, $R^3$=SC(O)N(CH$_3$)$_2$, $R^4$=Br, $R^5$=H, $R^6$=H, $R^7$=SCH$_3$, $R^8$=H, $R^9$=COOH (85); $R^1$=H, $R^2$=OCH$_3$, $R^3$=SCH$_3$, $R^4$=Br, $R^5$=H, $R^6$=H, $R^7$=SCH$_3$, $R^8$=H, $R^9$=COOH (86); $R^1$=H, $R^2$=OCH$_3$, $R^3$=OH, $R^4$=Br, $R^5$=H, $R^6$=H, $R^7$=SCH$_3$, $R^8$=H, $R^9$=H (87); =H, $R^2$=OCH$_3$, $R^3$=OC(S)N(CH$_3$)$_2$, $R^4$=Br, $R^5$=H, $R^6$=H, $R^7$=SCH$_3$, $R^8$=H, $R^9$=H (88); $R^1$=H, $R^2$=OCH$_3$, $R^3$=SC(O)N(CH$_3$)$_2$, $R^4$=Br, $R^5$=H, $R^6$=H, $R^7$=SCH$_3$, $R^8$=H, $R^9$=H (89); $R^1$=H, $R^2$=OCH$_3$, $R^3$=SCH$_3$, $R^4$=Br, $R^5$=H, $R^6$=H, $R^7$=SCH$_3$, $R^8$=H, $R^9$=H (90); =H, $R^2$=Br, $R^3$=OH, $R^4$=Br, $R^5$=H, $R^6$=H, $R^7$=SCH$_3$, $R^8$=H, $R^9$=COOH (91); $R^1$=H, $R^2$=Br, $R^3$=OC(S)N(CH$_3$)$_2$, $R^4$=Br, $R^5$=H, $R^6$=H, $R^7$=SCH$_3$, $R^8$=H, $R^9$=COOH (92); $R^1$=H, $R^2$=Br$_3$, $R^3$=SC(O)N(CH$_3$)$_2$, $R^4$=Br, $R^5$=H, $R^6$=H, $R^7$=SCH$_3$, $R^8$=H, $R^9$=COOH (93); $R^1$=H, $R^2$=Br, $R^3$=SCH$_3$, $R^4$=Br, $R^5$=H, $R^6$=H, $R^7$=SCH$_3$, $R^8$=H, $R^9$=COOH (94); $R^1$=H, $R^2$=Br$_3$, $R^3$=OH, $R^4$=Br, $R^5$=H, $R^6$=H, $R^7$=SCH$_3$, $R^8$=H, $R^9$=H (95); $R^1$=H, $R^2$=Br, $R^3$=OC(S)N(CH$_3$)$_2$, $R^4$=Br, $R^5$=H, $R^6$=H, $R^7$=SCH$_3$, $R^8$=H, $R^9$=H (96); $R^1$=H, $R^2$=Br, $R^3$=SC(O)N(CH$_3$)$_2$, $R^4$=Br, $R^5$=H, $R^6$=H, $R^7$=SCH$_3$, $R^8$=H, $R^9$=H (97); $R^1$=H, $R^2$=Br, $R^3$=SCH$_3$, $R^4$=Br, $R^5$=H, $R^6$=H, $R^7$=SCH$_3$, $R^8$=H, $R^9$=H (98); $R^1$=H, $R^2$=OCH$_3$, $R^3$=OH, $R^4$=OCH$_3$, $R^5$=H, $R^6$=SCH$_3$, $R^7$=H, $R^8$=H, $R^9$=COOH (99); $R^1$=H, $R^2$=OCH$_3$, $R^3$=OC(S)N(CH$_3$)$_2$, $R^4$=OCH$_3$, $R^5$=H, $R^6$=SCH$_3$, $R^7$=H, $R^8$=H, $R^9$=COOH (100); $R^1$=H, $R^2$=OCH$_3$, $R^3$=SC(O)N(CH$_3$)$_2$, $R^4$=OCH$_3$, $R^5$=H, $R^6$=SCH$_3$, $R^7$=H, $R^8$=H, $R^9$=COOH (101); $R^1$=H, $R^2$=OCH$_3$, $R^3$=SCH$_3$, $R^4$=OCH$_3$, $R^5$=H, $R^6$=SCH$_3$, $R^7$=H, $R^8$=H, $R^9$=COOH (102); $R^1$=H, $R^2$=OCH$_3$, $R^3$=OH, $R^4$=OCH$_3$, $R^5$=H, $R^6$=SCH$_3$, $R^7$=H, $R^8$=H, $R^9$=H (103); $R^1$=H, $R^2$=OCH$_3$, $R^3$=OC(S)N(CH$_3$)$_2$, $R^4$=OCH$_3$, $R^5$=H, $R^6$=SCH$_3$, $R^7$=H, $R^8$=H, $R^9$=H (104); $R^1$=H, $R^2$=OCH$_3$, $R^3$=SC(O)N(CH$_3$)$_2$, $R^4$=OCH$_3$, $R^5$=H, $R^6$=SCH$_3$, $R^7$=H, $R^8$=H, $R^9$=H (105); $R^1$=H, $R^2$=OCH$_3$, $R^3$=SCH$_3$, $R^4$=OCH$_3$, $R^5$=H, $R^6$=SCH$_3$, $R^7$=H, $R^8$=H, $R^9$=H (106); $R^1$=H, $R^2$=OCH$_3$, $R^3$=OH, $R^4$=Br, $R^5$=H, $R^6$=SCH$_3$, $R^7$=H, $R^8$=H, $R^9$=COOH (107); =H, $R^2$=OCH$_3$, $R^3$=OC(S)N(CH$_3$)$_2$, $R^4$=Br, $R^5$=H, $R^6$=SCH$_3$, $R^7$=H, $R^8$=H, $R^9$=COOH (108); $R^1$=H, $R^2$=OCH$_3$, $R^3$=SC(O)N(CH$_3$)$_2$, $R^4$=Br, $R^5$=H, $R^6$=SCH$_3$, $R^7$=H, $R^8$=H, $R^9$=COOH (109); $R^1$=H, $R^2$=OCH$_3$, $R^3$=SCH$_3$, $R^4$=Br, $R^5$=H, $R^6$=SCH$_3$, $R^7$=H, $R^8$=H, $R^9$=COOH (110); $R^1$=H, $R^2$=OCH$_3$, $R^3$=OH, $R^4$=Br, $R^5$=H, $R^6$=SCH$_3$, $R^7$=H, $R^8$=H, $R^9$=H (111); $R^1$=H, $R^2$=OCH$_3$, $R^3$=OC(S)N(CH$_3$)$_2$, $R^4$=Br, $R^5$=H, $R^6$=SCH$_3$, $R^7$=H, $R^8$=H, $R^9$=H (112); $R^1$=H, $R^2$=OCH$_3$, $R^3$=SC(O)N(CH$_3$)$_2$, $R^4$=Br, $R^5$=H, $R^6$=SCH$_3$, $R^7$=H, $R^8$=H, $R^9$=H (113); $R^1$=H, $R^2$=OCH$_3$, $R^3$=SCH$_3$, $R^4$=Br, $R^5$=H, $R^6$=SCH$_3$, $R^7$=H, $R^8$=H, $R^9$=H (114); Fe=H, $R^2$=Br, $R^3$=OH, $R^4$=Br, $R^5$=H, $R^6$=SCH$_3$, $R^7$=H, $R^8$=H, $R^9$=COOH (115); $R^1$=H, $R^2$=Br, $R^3$=OC(S)N(CH$_3$)$_2$, $R^4$=Br, $R^5$=H, $R^6$=SCH$_3$, $R^7$=H, $R^8$=H, $R^9$=COOH; =H, $R^2$=Br$_3$, $R^3$=SC(O)N(CH$_3$)$_2$, $R^4$=Br, $R^5$=H, $R^6$=SCH$_3$, $R^7$=H, $R^8$=H, $R^9$=COOH (116); $R^1$=H, $R^2$=Br, $R^3$=SCH$_3$, $R^4$=Br, $R^5$=H, $R^6$=SCH$_3$, $R^7$=H, $R^8$=H, $R^9$=COOH (117); $R^1$=H, $R^2$=Br$_3$, $R^3$=OH, $R^4$=Br, $R^5$=H, $R^6$=SCH$_3$, $R^7$=H, $R^8$=H, $R^9$=H (118); $R^1$=H, $R^2$=Br, $R^3$=OC(S)N(CH$_3$)$_2$, $R^4$=Br, $R^5$=H, $R^6$=SCH$_3$, $R^7$=H, $R^8$=H, $R^9$=H (119); $R^1$=H, $R^2$=Br, $R^3$=SC(O)N(CH$_3$)$_2$, $R^4$=Br, $R^5$=H, $R^6$=SCH$_3$, $R^7$=H, $R^8$=H, $R^9$=H (120); $R^1$=H, $R^2$=Br, $R^3$=SCH$_3$, $R^4$=Br, $R^5$=H, $R^6$=SCH$_3$, $R^7$=H, $R^8$=H, $R^9$=H (121); $R^1$=H, $R^2$=OCH$_3$, $R^3$=OC(S)N(CH$_3$)$_2$, $R^4$=OCH$_3$, $R^5$=H, $R^6$=OCH$_3$, $R^7$=OCH$_3$, $R^8$=H, $R^9$=COOH (122); $R^1$=H, $R^2$=OCH$_3$, $R^3$=SC(O)N(CH$_3$)$_2$, $R^4$=OCH$_3$, $R^5$=H, $R^6$=OCH$_3$, $R^7$=OCH$_3$, $R^8$=H, $R^9$=COOH (123); $R^1$=H, $R^2$=OCH$_3$, $R^3$=SCH$_3$, $R^4$=OCH$_3$, $R^5$=H, $R^6$=OCH$_3$, $R^7$=OCH$_3$, $R^8$=H, $R^9$=COOH (124); $R^1$=H, $R^2$=OCH$_3$, $R^3$=OC(S)N(CH$_3$)$_2$, $R^4$=OCH$_3$, $R^5$=H, $R^6$=OCH$_3$, $R^7$=OCH$_3$, $R^8$=H, $R^9$=H (125); =H, $R^2$=OCH$_3$, $R^3$=SC(O)N(CH$_3$)$_2$, $R^4$=OCH$_3$, $R^5$=H, $R^6$=OCH$_3$, $R^7$=OCH$_3$, $R^8$=H, $R^9$=H (126); $R^1$=H, $R^2$=OCH$_3$, $R^3$=SCH$_3$, $R^4$=OCH$_3$, $R^5$=H, $R^6$=OCH$_3$, $R^7$=OCH$_3$, $R^8$=H, $R^9$=H (127); $R^1$=H, $R^2$=OCH$_3$, $R^3$=OC(S)N(CH$_3$)$_2$, $R^4$=Br, $R^5$=H, $R^6$=OCH$_3$, $R^7$=OCH$_3$, $R^8$=H, $R^9$=COOH (128); $R^1$=H, $R^2$=OCH$_3$, $R^3$=SC(O)N(CH$_3$)$_2$, $R^4$=Br, $R^5$=H, $R^6$=OCH$_3$, $R^7$=OCH$_3$, $R^8$=H, $R^9$=COOH (129); $R^1$=H, $R^2$=OCH$_3$, $R^3$=SCH$_3$, $R^4$=Br, $R^5$=H, $R^6$=OCH$_3$, $R^7$=OCH$_3$, $R^8$=H, $R^9$=COOH (130); $R^1$=H, $R^2$=OCH$_3$, $R^3$=OC(S)N(CH$_3$)$_2$, $R^4$=Br, $R^5$=H, $R^6$=OCH$_3$, $R^7$=OCH$_3$, $R^8$=H, $R^9$=H (131); $R^1$=H, $R^2$=OCH$_3$, $R^3$=SC(O)N(CH$_3$)$_2$, $R^4$=Br, $R^5$=H, $R^6$=OCH$_3$, $R^7$=OCH$_3$, $R^8$=H, $R^9$=H (132); $R^1$=H, $R^2$=OCH$_3$, $R^3$=SCH$_3$, $R^4$=Br, $R^5$=H, $R^6$=OCH$_3$, $R^7$=OCH$_3$, $R^8$=H, $R^9$=H (133); $R^1$=H, $R^2$=Br, $R^3$=OC(S)N(CH$_3$)$_2$, $R^4$=Br, $R^5$=H, $R^6$=OCH$_3$, $R^7$=OCH$_3$, $R^8$=H, $R^9$=COOH (134); $R^1$=H, $R^2$=Br, $R^3$=SC(O)N(CH$_3$)$_2$, $R^4$=Br, $R^5$=H, $R^6$=OCH$_3$, $R^7$=OCH$_3$, $R^8$=H, $R^9$=COOH (135); $R^1$=H, $R^2$=Br, $R^3$=SCH$_3$, $R^4$=Br, $R^5$=H, $R^6$=OCH$_3$, $R^7$=OCH$_3$, $R^8$=H, $R^9$=COOH (136); $R^1$=H, $R^2$=Br, $R^3$=OC(S)N(CH$_3$)$_2$, $R^4$=Br, $R^5$=H, $R^6$=OCH$_3$, $R^7$=OCH$_3$, $R^8$=H, $R^9$=H (137); $R^1$=H, $R^2$=Br, $R^3$=SC(O)N(CH$_3$)$_2$, $R^4$=Br, $R^5$=H, $R^6$=OCH$_3$, $R^7$=OCH$_3$, $R^8$=H, $R^9$=H (138); $R^1$=H, $R^2$=Br, $R^3$=SCH$_3$, $R^4$=Br, $R^5$=H, $R^6$=OCH$_3$, $R^7$=OCH$_3$, $R^8$=H, $R^9$=H (139); $R^1$=H, $R^2$=OCH$_3$, $R^3$=OC(S)N(CH$_3$)$_2$, $R^4$=OCH$_3$, $R^5$=H, $R^6$=OCH$_3$, $R^7$=OH, $R^8$=H, $R^9$=COOH (140); $R^1$=H, $R^2$=OCH$_3$, $R^3$=SC(O)N(CH$_3$)$_2$, $R^4$=OCH$_3$, $R^5$=H, $R^6$=OCH$_3$, $R^7$=OH, $R^8$=H, $R^9$=COOH (141); $R^1$=H, $R^2$=OCH$_3$, $R^3$=SCH$_3$, $R^4$=OCH$_3$, $R^5$=H, $R^6$=OCH$_3$, $R^7$=OH, $R^8$=H, $R^9$=COOH (142); $R^1$=H, $R^2$=OCH$_3$, $R^3$=OC(S)N(CH$_3$)$_2$, $R^4$=OCH$_3$, $R^5$=H, $R^6$=OCH$_3$, $R^7$=OH, $R^8$=H, $R^9$=H (143); $R^1$=H, $R^2$=OCH$_3$, $R^3$=SC(O)N(CH$_3$)$_2$, $R^4$=OCH$_3$, $R^5$=H, $R^6$=OCH$_3$, $R^7$=OH, $R^8$=H, $R^9$=H (144); $R^1$=H, $R^2$=OCH$_3$, $R^3$=SCH$_3$, $R^4$=OCH$_3$, $R^5$=H, $R^6$=OCH$_3$, $R^7$=OH, $R^8$=H, $R^9$=H (145); $R^1$=H, $R^2$=OCH$_3$, $R^3$=OC(S)N(CH$_3$)$_2$, $R^4$=Br, $R^5$=H, $R^6$=OCH$_3$, $R^7$=OH, $R^8$=H, $R^9$=COOH (146); $R^1$=H, $R^2$=OCH$_3$, $R^3$=SC(O)N(CH$_3$)$_2$, $R^4$=Br, $R^5$=H, $R^6$=OCH$_3$, $R^7$=OH, $R^8$=H, $R^9$=COOH (147); $R^1$=H, $R^2$=OCH$_3$, $R^3$=SCH$_3$, $R^4$=Br, $R^5$=H, $R^6$=OCH$_3$, $R^7$=OH, $R^8$=H, $R^9$=COOH (148); $R^1$=H, $R^2$=OCH$_3$, $R^3$=OC(S)N(CH$_3$)$_2$, $R^4$=Br, $R^5$=H, $R^6$=OCH$_3$, $R^7$=OH, $R^8$=H, $R^9$=H (149); $R^1$=H, $R^2$=OCH$_3$, $R^3$=SC(O)N(CH$_3$)$_2$, $R^4$=Br, $R^5$=H, $R^6$=OCH$_3$, $R^7$=OH, $R^8$=H, $R^9$=H (150); $R^1$=H, $R^2$=OCH$_3$, $R^3$=SCH$_3$, $R^4$=Br, $R^5$=H, $R^6$=OCH$_3$, $R^7$=OH, $R^8$=H, $R^9$=H (151); =H, $R^2$=Br, $R^3$=OC(S)N(CH$_3$)$_2$, $R^4$=Br, $R^5$=H, $R^6$=OCH$_3$, $R^7$=OH, $R^8$=H, $R^9$=COOH (152); $R^1$=H, $R^2$=Br, $R^3$=SC(O)N(CH$_3$)$_2$, $R^4$=Br, $R^5$=H, $R^6$=OCH$_3$, $R^7$=OH, $R^8$=H, $R^9$=COOH (153); $R^1$=H, $R^2$=Br, $R^3$=SCH$_3$, $R^4$=Br, $R^5$=H, $R^6$=OCH$_3$, $R^7$=OH, $R^8$=H, $R^9$=COOH (154); $R^1$=H, $R^2$=Br, $R^3$=OC(S)N(CH$_3$)$_2$, $R^4$=Br, $R^5$=H, $R^6$=OCH$_3$, $R^7$=OH, $R^8$=H, $R^9$=H (155); $R^1$=H, $R^2$=Br, $R^3$=SC(O)N(CH$_3$)$_2$, $R^4$=Br, $R^5$=H, $R^6$=OCH$_3$, $R^7$=OH, $R^8$=H, $R^9$=H (156); =H, $R^2$=Br, $R^3$=SCH$_3$, $R^4$=Br, $R^5$=H, $R^6$=OCH$_3$, $R^7$=OH, $R^8$=H, $R^9$=H (157).

According to the first aspect, the invention also relates to the new 4,5-diphenyl-1,3-oxazole derivatives of general formula 2, (2)

wherein:
$R^1$=OCH$_3$, $R^2$=OCH$_3$, $R^3$=OCH$_3$, $R^4$=H, $R^5$=H, $R^6$=SCH$_3$ (158); $R^1$=OCH$_3$, $R^2$=SCH$_3$, $R^3$=OCH$_3$, $R^4$=H, $R^5$=H, $R^6$=SCH$_3$ (159); $R^1$=Br, $R^2$=OCH$_3$, $R^3$=OCH$_3$, $R^4$=H, $R^5$=H, $R^6$=SCH$_3$ (160); $R^1$=Br, $R^2$=SCH$_3$, $R^3$=OCH$_3$, $R^4$=H, $R^5$=H, $R^6$=SCH$_3$ (161); $R^1$=Br, $R^2$=OCH$_3$, $R^3$=Br, $R^4$=H, $R^5$=H, $R^6$=SCH$_3$ (162); $R^1$=Br, $R^2$=SCH$_3$, $R^3$=Br, $R^4$=H, $R^5$=H, $R^6$=SCH$_3$ (163); Fe=OCH$_3$, $R^2$=SCH$_3$, $R^3$=OCH$_3$, $R^4$=H, $R^5$=H, $R^6$=OCH$_3$ (164); $R^1$=Br, $R^2$=SCH$_3$, $R^3$=OCH$_3$, $R^4$=H, $R^5$=H, $R^6$=OCH$_3$ (165); $R^1$=Br, $R^2$=SCH$_3$, $R^3$=Br, $R^4$=H, $R^5$=H, $R^6$=OCH$_3$ (166); $R^1$=OCH$_3$, $R^2$=SCH$_3$, $R^3$=OCH$_3$, $R^4$=H, $R^5$=OCH$_3$, $R^6$=H (167); $R^1$=Br, $R^2$=SCH$_3$, $R^3$=OCH$_3$, $R^4$=H, $R^5$=OCH$_3$, $R^6$=H (168); $R^1$=Br, $R^2$=SCH$_3$, $R^3$=Br, $R^4$=H, $R^5$=OCH$_3$, $R^6$=H (169); $R^1$=OCH$_3$, $R^2$=SCH$_3$, $R^3$=OCH$_3$, $R^4$=OCH$_3$, $R^5$=H, $R^6$=H (170); $R^1$=Br, $R^2$=SCH$_3$, $R^3$=OCH$_3$, $R^4$=OCH$_3$, $R^5$=H, $R^6$=H (171); $R^1$=Br, $R^2$=SCH$_3$, $R^3$=Br, $R^4$=OCH$_3$, $R^5$=H, $R^6$=H (172); $R^1$=OCH$_3$, $R^2$=SCH$_3$, $R^3$=OCH$_3$, $R^4$=SCH$_3$, $R^5$=H, $R^6$=H (173); $R^1$=Br, $R^2$=SCH$_3$, $R^3$=OCH$_3$, $R^4$=SCH$_3$, $R^5$=H, $R^6$=H (174); $R^1$=Br, $R^2$=OCH$_3$, $R^3$=Br, $R^4$=SCH$_3$, $R^5$=H, $R^6$=H (175); $R^1$=Br, $R^2$=SCH$_3$, $R^3$=Br, $R^4$=SCH$_3$, $R^5$=H, $R^6$=H (176); $R^1$=OCH$_3$, $R^2$=OCH$_3$, $R^3$=OCH$_3$, $R^4$=H, $R^5$=OCH$_3$, $R^6$=SCH$_3$ (178); $R^1$=OCH$_3$, $R^2$=SCH$_3$, $R^3$=OCH$_3$, $R^4$=H, $R^5$=OCH$_3$, $R^6$=SCH$_3$ (179); $R^1$=Br, $R^2$=OCH$_3$, $R^3$=OCH$_3$, $R^4$=H, $R^5$=OCH$_3$, $R^6$=SCH$_3$ (180); $R^1$=Br, $R^2$=SCH$_3$, $R^3$=OCH$_3$, $R^4$=H, $R^5$=OCH$_3$, $R^6$=SCH$_3$ (181); $R^1$=Br, $R^2$=OCH$_3$, $R^3$=Br, $R^4$=H, $R^5$=OCH$_3$, $R^6$=SCH$_3$ (182); =Br, $R^2$=SCH$_3$, $R^3$=Br, $R^4$=H, $R^5$=OCH$_3$, $R^6$=SCH$_3$ (183); $R^1$=OCH$_3$, $R^2$=SCH$_3$, $R^3$=OCH$_3$, $R^4$=H, $R^5$=OCH$_3$, $R^6$=OCH$_3$ (184); $R^1$=Br, $R^2$=SCH$_3$, $R^3$=OCH$_3$, $R^4$=H, $R^5$=OCH$_3$, $R^6$=OCH$_3$ (185); $R^1$=Br, $R^2$=SCH$_3$, $R^3$=Br, $R^4$=H, $R^5$=OCH$_3$, $R^6$=OCH$_3$ (186); $R^1$=OCH$_3$, $R^2$=OCH$_3$, $R^3$=OCH$_3$, $R^4$=OCH$_3$, $R^5$=SCH$_3$, $R^6$=H (187); $R^1$=OCH$_3$, $R^2$=SCH$_3$, $R^3$=OCH$_3$, $R^4$=OCH$_3$, $R^5$=SCH$_3$, $R^6$=H (188); $R^1$=Br, $R^2$=OCH$_3$, $R^3$=OCH$_3$, $R^4$=OCH$_3$, $R^5$=SCH$_3$, $R^6$=H (189); $R^1$=Br, $R^2$=SCH$_3$, $R^3$=OCH$_3$, $R^4$=OCH$_3$, $R^5$=SCH$_3$, $R^6$=H (190); $R^1$=Br, $R^2$=OCH$_3$, $R^3$=Br, $R^4$=OCH$_3$, $R^5$=SCH$_3$, $R^6$=H (191); =Br, $R^2$=SCH$_3$, $R^3$=Br, $R^4$=OCH$_3$, $R^5$=SCH$_3$, $R^6$=H (192); $R^1$=OCH$_3$, $R^2$=OCH$_3$, $R^3$=OCH$_3$, $R^4$=SCH$_3$, $R^5$=OCH$_3$, $R^6$=H (193); $R^1$=OCH$_3$, $R^2$=SCH$_3$, $R^3$=OCH$_3$, $R^4$=SCH$_3$, $R^5$=OCH$_3$, $R^6$=H (194); $R^1$=Br, $R^2$=OCH$_3$, $R^3$=OCH$_3$, $R^4$=SCH$_3$, $R^5$=OCH$_3$, $R^6$=H (195); $R^1$=Br, $R^2$=SCH$_3$, $R^3$=OCH$_3$, $R^4$=SCH$_3$, $R^5$=OCH$_3$, $R^6$=H (196); =Br, $R^2$=OCH$_3$, $R^3$=Br, $R^4$=SCH$_3$, $R^5$=OCH$_3$, $R^6$=H (197); =Br, $R^2$=SCH$_3$, $R^3$=Br, $R^4$=SCH$_3$, $R^5$=OCH$_3$, $R^6$=H (198); $R^1$=OCH$_3$, $R^2$=SCH$_3$, $R^3$=OCH$_3$, $R^4$=OCH$_3$, $R^5$=OCH$_3$, $R^6$=H (199); $R^1$=Br, $R^2$=SCH$_3$, $R^3$=OCH$_3$, $R^4$=OCH$_3$, $R^5$=OCH$_3$, $R^6$=H (200); $R^1$=Br, $R^2$=SCH$_3$, $R^3$=Br, $R^4$=OCH$_3$, $R^5$=OCH$_3$, $R^6$=H (201); $R^1$=OCH$_3$, $R^2$=SCH$_3$, $R^3$=OCH$_3$, $R^4$=OCH$_3$, $R^5$=NO$_2$, $R^6$=H (202); $R^1$=Br, $R^2$=SCH$_3$, $R^3$=OCH$_3$, $R^4$=OCH$_3$, $R^5$=NO$_2$, $R^6$=H (203); $R^1$=Br, $R^2$=SCH$_3$, $R^3$=Br, $R^4$=OCH$_3$, $R^5$=NO$_2$, $R^6$=H (204); $R^1$=OCH$_3$, $R^2$=SCH$_3$, $R^3$=OCH$_3$, $R^4$=OCH$_3$, $R^5$=NH$_2$, $R^6$=H (205); $R^1$=Br, $R^2$=SCH$_3$, $R^3$=OCH$_3$, $R^4$=OCH$_3$, $R^5$=NH$_2$, $R^6$=H (206); $R^1$=Br, $R^2$=SCH$_3$, $R^3$=Br, $R^4$=OCH$_3$, $R^5$=NH$_2$, $R^6$=H (207); $R^1$=OCH$_3$, $R^2$=SCH$_3$, $R^3$=OCH$_3$, $R^4$=OCH$_3$, $R^5$=NHC(O)CH(NH$_2$)CH$_2$OH, $R^6$=H (208); $R^1$=Br, $R^2$=SCH$_3$, $R^3$=OCH$_3$, $R^4$=OCH$_3$, $R^5$=NHC(O)CH(NH$_2$)CH$_2$OH, $R^6$=H (209); $R^1$=Br, $R^2$=SCH$_3$, $R^3$=Br, $R^4$=OCH$_3$, $R^5$=NHC(O)CH(NH$_2$)CH$_2$OH, $R^6$=H (210).

According to the first aspect, the invention finally relates to the new 1-methyl-4,5-diphenyl-1H-imidazole derivatives of general formula 3,

(3)

wherein:
$R^1$=OCH$_3$, $R^2$=OCH$_3$, $R^3$=OCH$_3$, $R^4$=H, $R^5$=H, $R^6$=SCH$_3$ (211); $R^1$=OCH$_3$, $R^2$=SCH$_3$, $R^3$=OCH$_3$, $R^4$=H, $R^5$=H, $R^6$=SCH$_3$ (212); $R^1$=Br, $R^2$=OCH$_3$, $R^3$=OCH$_3$, $R^4$=H, $R^5$=H, $R^6$=SCH$_3$ (213); $R^1$=Br, $R^2$=SCH$_3$, $R^3$=OCH$_3$, $R^4$=H, $R^5$=H, $R^6$=SCH$_3$ (214); $R^1$=Br, $R^2$=OCH$_3$, $R^3$=Br, $R^4$=H, $R^5$=H, $R^6$=SCH$_3$ (215); $R^1$=Br, $R^2$=SCH$_3$, $R^3$=Br, $R^4$=H, $R^5$=H, $R^6$=SCH$_3$ (216); $R^1$=OCH$_3$, $R^2$=SCH$_3$, $R^3$=OCH$_3$, $R^4$=H, $R^5$=H, $R^6$=OCH$_3$ (217); $R^1$=Br, $R^2$=SCH$_3$, $R^3$=OCH$_3$, $R^4$=H, $R^5$=H, $R^6$=OCH$_3$ (218); $R^1$=Br, $R^2$=SCH$_3$, $R^3$=Br, $R^4$=H, $R^5$=H, $R^6$=OCH$_3$ (219); $R^1$=OCH$_3$, $R^2$=SCH$_3$, $R^3$=OCH$_3$, $R^4$=H, $R^5$=OCH$_3$, $R^6$=H (220); $R^1$=Br, $R^2$=SCH$_3$, $R^3$=OCH$_3$, $R^4$=H, $R^5$=OCH$_3$, $R^6$=H (221); $R^1$=Br, $R^2$=SCH$_3$, $R^3$=Br, $R^4$=H, $R^5$=OCH$_3$, $R^6$=H (222); $R^1$=OCH$_3$, $R^2$=SCH$_3$, $R^3$=OCH$_3$, $R^4$=OCH$_3$, $R^5$=H, $R^6$=H (223); $R^1$=Br, $R^2$=SCH$_3$, $R^3$=OCH$_3$, $R^4$=OCH$_3$, $R^5$=H, $R^6$=H (224); $R^1$=Br, $R^2$=SCH$_3$, $R^3$=Br, $R^4$=OCH$_3$, $R^5$=H, $R^6$=H (225); $R^1$=OCH$_3$, $R^2$=SCH$_3$, $R^3$=OCH$_3$, $R^4$=SCH$_3$, $R^5$=H, $R^6$=H (226); $R^1$=Br, $R^2$=OCH$_3$, $R^3$=OCH$_3$, $R^4$=SCH$_3$, $R^5$=H, $R^6$=H (227); $R^1$=Br, $R^2$=SCH$_3$, $R^3$=OCH$_3$, $R^4$=SCH$_3$, $R^5$=H, $R^6$=H (228); $R^1$=Br, $R^2$=OCH$_3$, $R^3$=Br, $R^4$=SCH$_3$, $R^5$=H, $R^6$=H (229); =Br, $R^2$=SCH$_3$, $R^3$=Br, $R^4$=SCH$_3$, $R^5$=H, $R^6$=H (230); $R^1$=OCH$_3$, $R^2$=OCH$_3$, $R^3$=OCH$_3$, $R^4$=H, $R^5$=OCH$_3$, $R^6$=SCH$_3$ (231); $R^1$=OCH$_3$, $R^2$=SCH$_3$, $R^3$=OCH$_3$, $R^4$=H, $R^5$=OCH$_3$, $R^6$=SCH$_3$ (232); $R^1$=Br, $R^2$=OCH$_3$, $R^3$=OCH$_3$, $R^4$=H, $R^5$=OCH$_3$, $R^6$=SCH$_3$ (233); $R^1$=Br, $R^2$=SCH$_3$, $R^3$=OCH$_3$, $R^4$=H, $R^5$=OCH$_3$, $R^6$=SCH$_3$ (234); $R^1$=Br, $R^2$=OCH$_3$, $R^3$=Br, $R^4$=H, $R^5$=OCH$_3$, $R^6$=SCH$_3$ (235); $R^1$=Br, $R^2$=SCH$_3$, $R^3$=Br, $R^4$=H, $R^5$=OCH$_3$, $R^6$=SCH$_3$ (236); $R^1$=OCH$_3$, $R^2$=SCH$_3$, $R^3$=OCH$_3$, $R^4$=H, $R^5$=OCH$_3$, $R^6$=OCH$_3$ (237); $R^1$=Br, $R^2$=SCH$_3$, $R^3$=OCH$_3$, $R^4$=H, $R^5$=OCH$_3$, $R^6$=OCH$_3$ (238); $R^1$=Br, $R^2$=SCH$_3$, $R^3$=Br, $R^4$=H, $R^5$=OCH$_3$, $R^6$=OCH$_3$ (239); $R^1$=OCH$_3$, $R^2$=OCH$_3$, $R^3$=OCH$_3$, $R^4$=OCH$_3$, $R^5$=SCH$_3$, $R^6$=H (240); $R^1$=OCH$_3$, $R^2$=SCH$_3$, $R^3$=OCH$_3$, $R^4$=OCH$_3$, $R^5$=SCH$_3$, $R^6$=H (241); $R^1$=Br, $R^2$=OCH$_3$, $R^3$=OCH$_3$, $R^4$=OCH$_3$, $R^5$=SCH$_3$, $R^6$=H (242); $R^1$=Br, $R^2$=SCH$_3$, $R^3$=OCH$_3$, $R^4$=OCH$_3$, $R^5$=SCH$_3$, $R^6$=H (243); $R^1$=Br, $R^2$=OCH$_3$, $R^3$=Br, $R^4$=OCH$_3$, $R^5$=SCH$_3$, $R^6$=H (244); $R^1$=Br, $R^2$=SCH$_3$, $R^3$=Br, $R^4$=OCH$_3$, $R^5$=SCH$_3$, $R^6$=H (245); $R^1$=OCH$_3$, $R^2$=OCH$_3$, $R^3$=OCH$_3$, $R^4$=SCH$_3$, $R^5$=OCH$_3$, $R^6$=H (246); $R^1$=OCH$_3$, $R^2$=SCH$_3$, $R^3$=OCH$_3$, $R^4$=SCH$_3$, $R^5$=OCH$_3$, $R^6$=H (247); =Br, $R^2$=OCH$_3$, $R^3$=OCH$_3$, $R^4$=SCH$_3$, $R^5$=OCH$_3$, $R^6$=H (248); $R^1$=Br, $R^2$=SCH$_3$, $R^3$=OCH$_3$, $R^4$=SCH$_3$, $R^5$=OCH$_3$, $R^6$=H (249); $R^1$=Br, $R^2$=OCH$_3$, $R^3$=Br, $R^4$=SCH$_3$, $R^5$=OCH$_3$, $R^6$=H (250); =Br, $R^2$=SCH$_3$, $R^3$=Br, $R^4$=SCH$_3$, $R^5$=OCH$_3$, $R^6$=H (251); $R^1$=OCH$_3$, $R^2$=SCH$_3$, $R^3$=OCH$_3$, $R^4$=OCH$_3$, $R^5$=OCH$_3$, $R^6$=H (252); $R^1$=Br, $R^2$=SCH$_3$, $R^3$=OCH$_3$, $R^4$=OCH$_3$, $R^5$=OCH$_3$, $R^6$=H (253); $R^1$=Br, $R^2$=SCH$_3$, $R^3$=Br, $R^4$=OCH$_3$, $R^5$=OCH$_3$, $R^6$=H (254); $R^1$=OCH$_3$, $R^2$=SCH$_3$, $R^3$=OCH$_3$, $R^4$=OCH$_3$, $R^5$=NO$_2$, $R^6$=H (255); $R^1$=Br, $R^2$=SCH$_3$, $R^3$=OCH$_3$, $R^4$=OCH$_3$, $R^5$=NO$_2$, $R^6$=H (256); $R^1$=Br, $R^2$=SCH$_3$, $R^3$=Br, $R^4$=OCH$_3$, $R^5$=NO$_2$, $R^6$=H (257); $R^1$=OCH$_3$, $R^2$=SCH$_3$, $R^3$=OCH$_3$, $R^4$=OCH$_3$, $R^5$=NH$_2$, $R^6$=H (258); $R^1$=Br, $R^2$=SCH$_3$, $R^3$=OCH$_3$, $R^4$=OCH$_3$, $R^5$=NH$_2$, $R^6$=H (259); $R^1$=Br, $R^2$=SCH$_3$, $R^3$=Br, $R^4$=OCH$_3$, $R^5$=NH$_2$, $R^6$=H (260); $R^1$=OCH$_3$, $R^2$=SCH$_3$, $R^3$=OCH$_3$, $R^4$=OCH$_3$, $R^5$=NHC(O)CH(NH$_2$)CH$_2$OH, $R^6$=H (261); $R^1$=Br, $R^2$=SCH$_3$, $R^3$=OCH$_3$, $R^4$=OCH$_3$, $R^5$=NHC(O)CH(NH$_2$)CH$_2$OH, $R^6$=H (262); $R^1$=Br, $R^2$=SCH$_3$, $R^3$=Br, $R^4$=OCH$_3$, $R^5$=NHC(O)CH(NH$_2$)CH$_2$OH, $R^6$=H (263).

The new derivatives, according to the invention, are also compounds of general formula 2 or 3, wherein $R^1$, $R^2$, $R^3$, $R^4$, $R^5$, $R^6$ have above-mentioned meaning, which are pharmaceutically acceptable salts, in particular chlorides, bromides, phosphates, hydrogen sulphates (VI), sulphates (VI), acetates, citrates, tartrates and lactates.

The new derivatives of cis-stilbene were prepared using the Perkin method of stereoselective condensation (scheme 1) between suitable phenylacetate acid and benzoic aldehyde (Gaukroger, K.; Hadfield, J. A.; Hepworth, L. A.; Lawrence, N. J.; McGown, A. T. *J. Org. Chem.* 2001, 66, 8135-8138). The reaction is carried out in acetic anhydride with addition of triethylamine as a catalyst at the boiling point of the reaction mixture. The obtained α-phenylcinnamic acid is decarboxylated in quinoline with the addition of copper as a catalyst at a temperature of about 220° C. The final product is isolated by known chromatographic techniques with the use of a suitably chosen eluent.

scheme 1

The synthesis of new derivatives of 4,5-diphenyl-1,3-oxazole and 1-methyl-4,5-diphenyl-1H-imidazole (scheme 2) was performed by known synthetic routes (Wang, L.; Woods, K. W.; Li, Q.; Barr, K. J.; McCroskey, R. W.; Hannick, S. M.; Gherke, L.; Bruce Credo, R.; Hui, Y.; Marsh, K. et al. J. Med. Chem. 2002, 45, 1697-1711. Schobert, R.; Biersack, B.; Dietrich, A.; Effenberger-Neidnicht, K.; Knauer, S.; Mueller, T. J. Med. Chem. 2010, 53, 6595-6602) using the previously obtained p-tosylmethyl isocyanides (TosMICs). The latter is prepared by a two-step procedure involving a reaction between suitable benzoic aldehydes and benzoic acids in the presence of p-toluenesulfonic acid and (+)camphorsulfonic acid (CSA) as a catalyst followed by reaction of formamides with phosphorus oxychloride in a dimethoxyethane environment.

$K_2CO_3$. The same TosMICs are used to obtain new derivatives of 1-methyl-4,5-diphenyl-1H-imidazole by the reaction with suitable benzoic aldehydes and methylamine in the presence of catalytic amounts of acetic acid.

Appropriate reactants, particularly phenylacetic acids and benzoic aldehydes, were commercially purchased or prepared by means of known methods.

In a second aspect, the invention relates to an application of the new derivatives of general formula 1 or 2 or 3, wherein $R^1$, $R^2$, $R^3$, $R^4$, $R^5$, $R^6$, $R^7$, $R^8$, $R^9$ have above-mentioned meaning respectively, as a microtubule-interfering agents (MIAs) influence in the process of tubulin polymerization or depolymerisation. The new compounds comprising the (Z)-1,2-diphenylethene structure, because of scheme 2

Tos = tosyl

TosMICs are converted to new 4,5-diphenyloxazole derivatives by the reaction with suitable benzoic aldehydes in a mixture of ethanol, dimethoxyethane and anhydrous the potential antimitotic and antiangiogenic activity can be used as ingredients in preparations used in the treatment of cancer.

The following examples are given for the purpose of illustrating the present disclosure and should not be considered as limitation on the scope or spirit of the disclosure.

$^1$H and $^{13}$C-NMR spectra were recorded on a Bruker Avance II 400 and Bruker Avance III 500 spectrometers at ambient temperature and in $CDCl_3$ as a solvent. The chemical shifts δ are reported in ppm relative to tetramethylsilane (TMS) as an internal standard.

Example 1

(E)-3-(2-methylthiophenyl)-2-(3,4,5-trimethoxyphenyl)prop-2-enoic acid (1)

3,4,5-trimethoxyphenylacetic acid (0.450 g, 2 mmol), 2-methylthiobenzaldehyde (0.300 g, 2 mmol) and triethylamine (0.5 ml, 3.59 mmol) were added to the 5 ml of acetic anhydride. The mixture was refluxed for 2 hours, then cooled and treated with 6 ml of conc. HCl. The precipitate was filtered off, washed several times with water and then recrystallized from 92% ethanol. 0.28 g (38.8%) of product in form of yellow needles with melting point 192-194° C. was obtained.

$^1$H NMR (400 MHz, $CDCl_3$) δ 8.23 (s, 1H), 7.26 (d, J=8.8 Hz, 1H), 7.20 (t, J=8.2 Hz, 1H), 6.87 (t, J=8.0 Hz, 1H), 6.79 (d, J=8.2 Hz, 1H), 6.76 (s, 1H), 6.40 (s, 2H), 3.84 (s, 3H), 3.69 (s, 6H), 2.52 (s, 3H). $^{13}$C NMR (101 MHz, $CDCl_3$) δ 172.59, 153.01, 140.05, 139.46, 137.81, 133.68, 132.86, 129.89, 129.76, 129.26, 125.97, 124.75, 107.42, 104.86, 60.86, 56.03, 16.30.

Example 2

(Z)-1-(2-methylthiophenyl)-2-(3,4,5-trimethoxyphenyl)ethen (2)

The (E)-3-(2-methylthiophenyl)-2-(3,4,5-trimethoxyphenyl)prop-2-enoic acid (1) (0.2 g, 0.55 mmol) and copper (0.18 g, 2.86 mmol) were added to 5 ml of quinoline, then the mixture was heated at oil bath of temperature 200° C. for 2 hours. The reaction mixture was cooled down to room temperature, filtered and washed with 10 ml of diethyl ether and then treated with 5 ml of concentrated HCl. The ether layer was separated and the aqueous layer was extracted with 3×10 ml of diethyl ether. The combined ether layers were washed with 30 ml of saturated sodium carbonate, 30 ml of water and 30 ml of brine, dried over with anhydrous $MgSO_4$, filtered and evaporated under vacuum to obtain 0.464 g of brown oil. The separation was carried out on a chromatographic column in the system of hexane:ethyl acetate (10:4). A 0.157 g (90.2%) of product in the form of cream-colored crystals was obtained.

$^1$H NMR (500 MHz, $CDCl_3$) δ 7.28 (dd, J=9.7, 8.2 Hz, 2H), 7.23 (d, J=7.9 Hz, 1H), 7.08 (t, J=7.2 Hz, 1H), 6.67 (d, J=12.0 Hz, 1H), 6.59 (d, J=12.0 Hz, 1H), 6.41 (s, 2H), 3.83 (s, 3H), 3.62 (s, 6H), 2.50 (s, 3H). $^{13}$C NMR (126 MHz, $CDCl_3$) δ 152.70, 137.72, 137.30, 136.57, 131.96, 131.33, 129.51, 127.89, 127.69, 125.28, 124.72, 106.18, 60.86, 55.72, 15.62.

Example 3

N-[(toluene-4-sulfonyl)(3,4,5-trimethoxyphenyl)methyl]formamide 3,4,5-trimethoxybenzaldehyde (4.6 g, 23.44 mmol), p-toluenesulfonic acid (3.01 g, 19.29 mmol) and (+)-camphorsulfonic acid (0.110 g, 0.47 mmol) were added to 10 ml of form amide, then the mixture was heated at 60° C. for 16 hours under vigorous stirring. After cooling, the resulting precipitate was filtered off, washed with several portions of methanol and dried. 4.37 g (59%) of white crystalline product with melting point 155-157° C. was obtained.

3,4,5-trimethoxyphenyl(tosyl)methyl isocyanide

N-[(toluene-4-sulfonyl)(3,4,5-trimethoxyphenyl)methyl]formamide (4.17 g, 11 mmol) was suspended in 100 ml of dimethoxyethane and the mixture was cooled down to −10° C. Then, phosphorus oxychloride (3.07 ml, 33 mmol) was added and then triethylamine (7.67 ml, 55 mmol) dissolved in 10 mL of DME, was slowly added dropwise. The flask content was then stirred at −5° C. for 2 hours, then poured into ice/water mixture (250 ml) and subsequently extracted with 3×60 ml of ethyl acetate. The combined ethyl acetate extracts were washed with 10% solution of $NaHCO_3$, brine, and then dried with anhydrous $MgSO_4$, filtered and evaporated under reduced pressure. 3.0 g (75.5%) of the product were obtained as pale yellow crystals with melting point 104-105° C.

$^1$H NMR (400 MHz, $CDCl_3$) δ7.65 (d, J=8.1 Hz, 2H), 7.33 (d, J=8.1 Hz, 2H), 6.49 (s, 2H), 5.53 (s, 1H), 3.87 (s, 3H), 3.78 (s, 6H), 2.47 (s, 3H).

4-(3,4,5-trimethoxyphenyl)-5-(2-methylthiophenyl)oxazole (158)

3,4,5-trimethoxyphenyl(tosyl)methyl isocyanate (0.433 g, 1.2 mmol), 2-methylthiobenzaldehyde (0.152 g, 1.0 mmol) and anhydrous $K_2CO_3$ (0.33 g, 2.4 mmol) were added to a mixture of 10 ml of ethanol and 3 ml of DME, and then refluxed for 2 hours. After cooling down to room temperature, the mixture was concentrated under reduced pressure. Afterwards, it was treated with 50 ml of ethyl acetate, washed with water, brine solution, dried with anhydrous $MgSO_4$, filtered and evaporated under reduced pressure. The residue (0.645 g) was purified by means of column chromatography in a system of hexane:ethyl acetate (1:1). 0.222 g (60%) of the cream-coloured crystalline product was obtained.

$^1$H NMR (400 MHz, $CDCl_3$) δ 8.00 (s, 1H), 7.49-7.43 (m, 1H), 7.38 (d, J=7.6 Hz, 1H), 7.35 (d, J=7.3 Hz, 1H), 7.23 (t, J=8.1 Hz, 1H), 6.80 (s, 2H), 3.82 (s, 3H), 3.66 (s, 6H), 2.40 (s, 3H). $^{13}$C NMR (101 MHz, $CDCl_3$) δ 153.09, 150.17, 143.75, 140.98, 137.57, 135.88, 131.54, 130.61, 127.68, 126.61, 125.57, 124.85, 103.35, 60.80, 55.69, 15.61.

Example 4

1-methyl-4-(3,4,5-trimethoxyphenyl)-5-(2-methylthiophenyl)imidazole (211)

2-methylthiobenzaldehyde (0.152 g, 1.0 mmol), 33% solution of methylamine in ethanol (0.62 ml, 5 mmol) and acetic acid (0.3 ml, 5.25 mmol) were added to 15 ml of ethanol and refluxed for 2 hours. After cooling down to room temperature, 3,4,5-trimethoxypheny(tosyl)methyl isocyanide (example 3) dissolved in 10 ml of DME was added followed by anhydrous $K_2CO_3$ (0.552 g, 4 mmol). The mixture was refluxed for 3 hours and next, after cooling, concentrated under reduced pressure. Afterwards, it was treated with 50 ml of ethyl acetate, washed with water, brine solution, dried with anhydrous $MgSO_4$, filtered and evaporated under reduced pressure. The residue (0.578 g) was purified by column chromatography in ethyl acetate:methanol (19:1). 0.158 g (44.3%) of the product in the form of yellow oil was obtained.

$^1$H NMR (400 MHz, $CDCl_3$) δ 7.62 (s, 1H), 7.49-7.43 (m, 1H), 7.32 (d, J=8.0 Hz, 1H), 7.28-7.22 (m, 2H), 6.76 (s, 2H), 3.79 (s, 3H), 3.62 (s, 6H), 3.43 (s, 3H), 2.38 (s, 3H). $^{13}$C NMR (101 MHz, $CDCl_3$) δ 152.87, 141.79, 138.21, 137.22, 136.33, 132.04, 130.01, 128.98, 126.34, 124.97, 124.47, 102.40, 60.75, 55.52, 31.67, 14.8.

The invention claimed is:

1. The new 4,5-diphenyl-1,3-oxazole derivatives of the general formula 2, (2)

wherein:
$R^1$=$OCH_3$, $R^2$=$OCH_3$, $R^3$=$OCH_3$, $R^4$=H, $R^5$=H, $R^6$=$SCH_3$; $R^1$=$OCH_3$, $R^2$=$SCH_3$, $R^3$=$OCH_3$, $R^4$=H, $R^5$=H, and $R^6$=$SCH_3$; $R^1$=Br, $R^2$=$OCH_3$, $R^3$=$OCH_3$, $R^4$=H, $R^5$=H, and R6=$SCH_3$; $R^1$=Br, $R^2$=$SCH_3$, $R^3$=$OCH_3$, $R^4$=H, $R^5$=H, and $R^6$=$SCH_3$; $R^1$=Br, $R^2$=$OCH_3$, $R^3$=Br, $R^4$=H, $R^5$=H, $R^6$=$SCH_3$; $R^1$=Br, $R^2$=$SCH_3$, $R^3$=Br, $R^4$=H, $R^5$=H, and $R^6$=$SCH_3$; $R^1$=$OCH_3$, $R^2$=$SCH_3$, $R^3$=$OCH_3$, $R^4$=H, $R^5$=H, and $R^6$=$OCH_3$; $R^1$=Br, $R^2$=$SCH_3$, $R^3$=$OCH_3$, $R^4$=H, $R^5$=H, and $R^6$=$OCH_3$; $R^1$=Br, $R^2$=$SCH_3$, $R^3$=Br, $R^4$=H, $R^5$=H, and $R^6$=$OCH_3$; $R^1$=$OCH_3$, $R^2$=$SCH_3$, $R^3$=$OCH_3$, $R^4$=H, $R^5$=$OCH_3$, and $R^6$=H; $R^1$=Br, $R^2$=$SCH_3$, $R^3$=$OCH_3$, $R^4$=H, $R^5$=$OCH_3$, and $R^6$=H; $R^1$=Br, $R^2$=$SCH_3$, $R^3$=Br, $R^4$=H, $R^5$=$OCH_3$, and $R^6$=H; $R^1$=$OCH_3$, $R^2$=$SCH_3$, $R^3$=$OCH_3$, $R^4$=$OCH_3$, $R^5$=H, and $R^6$=H; $R^1$=Br, $R^2$=$SCH_3$, $R^3$=$OCH_3$, $R^4$=$OCH_3$, $R^5$=H, and $R^6$=H; $R^1$=Br, $R^2$=$SCH_3$, $R^3$=Br, $R^4$=$OCH_3$, $R^5$=H, and $R^6$=H; $R^1$=$OCH_3$, $R^2$=$SCH_3$, $R^3$=$OCH_3$, $R^4$=$SCH_3$, $R^5$=H, and $R^6$=H; $R^1$=Br, $R^2$=$SCH_3$, $R^3$=$OCH_3$, $R^4$=$SCH_3$, $R^5$=H, and $R^6$=H; $R^1$=Br, $R^2$=$OCH_3$, $R^3$=Br, $R^4$=$SCH_3$, $R^5$=H, and $R^6$=H; $R^1$=$OCH_3$, $R^2$=$OCH_3$, $R^3$=$OCH_3$, $R^4$=H, $R^5$=$OCH_3$, and $R^6$=$SCH_3$; $R^1$=$OCH_3$, $R^2$=$SCH_3$, $R^3$=$OCH_3$, $R^4$=H, $R^5$=$OCH_3$, and $R^6$=$SCH_3$; $R^1$=Br, $R^2$=$OCH_3$, $R^3$=$OCH_3$, $R^4$=H, $R^5$=$OCH_3$, and $R^6$=$SCH_3$; $R^1$=Br, $R^2$=$SCH_3$, $R^3$=$OCH_3$, $R^4$=H, $R^5$=$OCH_3$, and $R^6$=$SCH_3$; $R^1$=Br, $R^2$=$SCH_3$, $R^3$=Br, $R^4$=H, $R^5$=$OCH_3$, and $R^6$=$SCH_3$; $R^1$=$OCH_3$, $R^2$=$SCH_3$, $R^3$=$OCH_3$, $R^4$=H, $R^5$=$OCH_3$, and $R^6$=$OCH_3$; $R^1$=Br, $R^2$=$SCH_3$, $R^3$=$OCH_3$, $R^4$=H, $R^5$=$OCH_3$, and $R^6$=$OCH_3$; $R^1$=Br, $R^2$=$SCH_3$, $R^3$=Br, $R^4$=H, $R^5$=$OCH_3$, and $R^6$=$OCH_3$; $R^1$=$OCH_3$, $R^2$=$OCH_3$, $R^3$=$OCH_3$, $R^4$=$OCH_3$, $R^5$=$SCH_3$, and $R^6$=H; $R^1$=$OCH_3$, $R^2$=$SCH_3$, $R^3$=$OCH_3$, $R^4$=$OCH_3$, $R^5$=$SCH_3$, and $R^6$=H; $R^1$=Br, $R^2$=$OCH_3$, $R^3$=$OCH_3$, $R^4$=$OCH_3$, $R^5$=$SCH_3$, and R6=H; $R^1$=Br, $R^2$=$SCH_3$, $R^3$=$OCH_3$, $R^4$=$OCH_3$, $R^5$=$SCH_3$, and $R^6$=H; $R^1$=Br, $R^2$=$OCH_3$, $R^3$=Br, $R^4$=$OCH_3$, $R^5$=$SCH_3$, and $R^6$=H; $R^1$=Br, $R^2$=$SCH_3$, $R^3$=Br, $R^4$=$OCH_3$, $R^5$=$SCH_3$, and $R^6$=H; $R^1$=$OCH_3$, $R^2$=$OCH_3$, $R^3$=$OCH_3$, $R^4$=$SCH_3$, $R^5$=$OCH_3$, and $R^6$=H; $R^1$=$OCH_3$, $R^2$=$SCH_3$, $R^3$=$OCH_3$, $R^4$=$SCH_3$, $R^5$=$OCH_3$, and $R^6$=H; $R^1$=Br, $R^2$=$OCH_3$, $R^3$=$OCH_3$, $R^4$=$SCH_3$, $R^5$=$OCH_3$, and $R^6$=H; $R^1$=Br, $R^2$=$SCH_3$, $R^3$=$OCH_3$, $R^4$=$SCH_3$, $R^5$=$OCH_3$, and $R^6$=H; $R^1$=Br, $R^2$=$OCH_3$, $R^3$=Br, $R^4$=$SCH_3$, $R^5$=$OCH_3$, and $R^6$=H; $R^1$=Br, $R^2$=$SCH_3$, $R^3$=Br, $R^4$=$SCH_3$, $R^5$=$OCH_3$, and $R^6$=H; $R^1$=$OCH_3$, $R^2$SCH_3, $R^3$=$OCH_3$, $R^4$=$OCH_3$, $R^5$=$OCH_3$, and $R^6$=H; $R^1$=Br, $R^2$=$SCH_3$, $R^3$=$OCH_3$, $R^4$=$OCH_3$, $R^5$=$OCH_3$, and $R^6$=H; $R^1$=Br, $R^2$=$SCH_3$, $R^3$=Br, $R^4$=$OCH_3$, $R^5$=$OCH_3$, and $R^6$=H; $R^1$=$OCH_3$, $R^2$=$SCH_3$, $R^3$=$OCH_3$, $R^4$=$OCH_3$, $R^5$=$NO_2$, and $R^6$=H; $R^1$=Br, $R^2$=$SCH_3$, $R^3$=$OCH_3$, $R^4$=$OCH_3$, $R^5$=$NO_2$, and $R^6$=H; $R^1$=Br, $R^2$=$SCH_3$, $R^3$=Br, $R^4$=$OCH_3$, $R^5$=$NO_2$, and $R^6$=H; $R^1$=$OCH_3$, $R^2$=$SCH_3$, $R^3$=$OCH_3$, $R^4$=$OCH_3$, $R^5$=$NH_2$, and $R^6$=H; $R^1$=Br, $R^2$=$SCH_3$, $R^3$=$OCH_3$, $R^4$=$OCH_3$, $R^5$=$NH_2$, and $R^6$=H; $R^1$=Br, $R^2$=$SCH_3$, $R^3$=Br, $R^4$=$OCH_3$, $R^5$=$NH_2$, and $R^6$=H; $R^1$=$OCH_3$, $R^2$=$SCH_3$, $R^3$=$OCH_3$, $R^4$=$OCH_3$, $R^5$=$NHC(O)CH(NH_2)CH_2OH$, and $R^6$=H; $R^1$=Br, $R^2$=$SCH_3$, $R^3$=$OCH_3$, $R^4$=$OCH_3$, $R^5$=$NHC(O)CH(NH_2)CH_2OH$, and $R^6$=H; or $R^1$=Br, $R^2$=$SCH_3$, $R^3$=Br, $R^4$=$OCH_3$, $R^5$=$NHC(O)CH(NH_2)CH_2OH$, and $R^6$=H.

2. A pharmaceutically acceptable salt of a 4,5-diphenyl-1,3-oxazole derivative of the general formula 2, (2)

wherein:
$R^1$=$OCH_3$, $R^2$=$OCH_3$, $R^3$=$OCH_3$, $R^4$=H, $R^5$=H, $R^6$=$SCH_3$; $R^1$=$OCH_3$, $R^2$=$SCH_3$, $R^3$=$OCH_3$, $R^4$=H, $R^5$=H, and $R^6$=$SCH_3$; $R^1$=Br, $R^2$=$OCH_3$, $R^3$=$OCH_3$, $R^4$=H, $R^5$=H, and R6=$SCH_3$; $R^1$=Br, $R^2$=$SCH_3$, $R^3$=$OCH_3$, $R^4$=H, $R^5$=H, and $R^6$=$SCH_3$; $R^1$=Br, $R^2$=$OCH_3$, $R^3$=Br, $R^4$=H, $R^5$=H, $R^6$=$SCH_3$;

$R^1$=Br, $R^2$=SCH$_3$, $R^3$=Br, $R^4$=H, $R^5$=H, and $R^6$=SCH$_3$; $R^1$=OCH$_3$, $R^2$=SCH$_3$, $R^3$=OCH$_3$, $R^4$=H, $R^5$=H, and $R^6$=OCH$_3$; $R^1$=Br, $R^2$=SCH$_3$, $R^3$=OCH$_3$, $R^4$=H, $R^5$=H, and $R^6$=OCH$_3$; $R^1$=Br, $R^2$=SCH$_3$, $R^3$=Br, $R^4$=H, $R^5$=H, and $R^6$=OCH$_3$; $R^1$=OCH$_3$, $R^2$=SCH$_3$, $R^3$=OCH$_3$, $R^4$=H, $R^5$=OCH$_3$, and $R^6$=H; $R^1$=Br, $R^2$=SCH$_3$, $R^3$=OCH$_3$, $R^4$=H, $R^5$=OCH$_3$, and $R^6$=H; $R^1$=Br, $R^2$=SCH$_3$, $R^3$=Br, $R^4$=H, $R^5$=OCH$_3$, and $R^6$=H; $R^1$=OCH$_3$, $R^2$=SCH$_3$, $R^3$=OCH$_3$, $R^4$=OCH$_3$, $R^5$=H, and $R^6$=H; $R^1$=Br, $R^2$=SCH$_3$, $R^3$=OCH$_3$, $R^4$=OCH$_3$, $R^5$=H, and $R^6$=H; $R^1$=Br, $R^2$=SCH$_3$, $R^3$=Br, $R^4$=OCH$_3$, $R^5$=H, and $R^6$=H; $R^1$=OCH$_3$, $R^2$=SCH$_3$, $R^3$=OCH$_3$, $R^4$=SCH$_3$, $R^5$=H, and $R^6$=H; $R^1$=Br, $R^2$=SCH$_3$, $R^3$=OCH$_3$, $R^4$=SCH$_3$, $R^5$=H, and $R^6$=H; $R^1$=Br, $R^2$=OCH$_3$, $R^3$=Br, $R^4$=SCH$_3$, $R^5$=H, and $R^6$=H; $R^1$=Br, $R^2$=SCH$_3$, $R^3$=Br, $R^4$=SCH$_3$, $R^5$=H, and $R^6$=H; $R^1$=OCH$_3$, $R^2$=OCH$_3$, $R^3$=OCH$_3$, $R^4$=H, $R^5$=OCH$_3$, and $R^6$=SCH$_3$; $R^1$=OCH$_3$, $R^2$=SCH$_3$, $R^3$=OCH$_3$, $R^4$=H, $R^5$=OCH$_3$, and $R^6$=SCH$_3$; $R^1$=Br, $R^2$=OCH$_3$, $R^3$=OCH$_3$, $R^4$=H, $R^5$=OCH$_3$, and $R^6$=SCH$_3$; $R^1$=Br, $R^2$=SCH$_3$, $R^3$=OCH$_3$, $R^4$=H, $R^5$=OCH$_3$, and $R^6$=SCH$_3$; $R^1$=Br, $R^2$=OCH$_3$, $R^3$=Br, $R^4$=H, $R^5$=OCH$_3$, and $R^6$=SCH$_3$; $R^1$=Br, $R^2$=SCH$_3$, $R^3$=Br, $R^4$=H, $R^5$=OCH$_3$, and $R^6$=SCH$_3$; $R^1$=OCH$_3$, $R^2$=SCH$_3$, $R^3$=OCH$_3$, $R^4$=H, $R^5$=OCH$_3$, and $R^6$=OCH$_3$; $R^1$=Br, $R^2$=SCH$_3$, $R^3$=OCH$_3$, $R^4$=H, $R^5$=OCH$_3$, and $R^6$=OCH$_3$; $R^1$=Br, $R^2$=SCH$_3$, $R^3$=Br, $R^4$=H, $R^5$=OCH$_3$, and $R^6$=OCH$_3$; $R^1$=OCH$_3$, $R^2$=OCH$_3$, $R^3$=OCH$_3$, $R^4$=OCH$_3$, $R^5$=SCH$_3$, and $R^6$=H; $R^1$=OCH$_3$, $R^2$=SCH$_3$, $R^3$=OCH$_3$, $R^4$=OCH$_3$, $R^5$=SCH$_3$, and $R^6$=H; $R^1$=Br, $R^2$=OCH$_3$, $R^3$=OCH$_3$, $R^4$=OCH$_3$, $R^5$=SCH$_3$, and R6=H; $R^1$=Br, $R^2$=SCH$_3$, $R^3$=OCH$_3$, $R^4$=OCH$_3$, $R^5$=SCH$_3$, and $R^6$=H; $R^1$=Br, $R^2$=OCH$_3$, $R^3$=Br, $R^4$=OCH$_3$, $R^5$=SCH$_3$, and $R^6$=H; $R^1$=Br, $R^2$=SCH$_3$, $R^3$=Br, $R^4$=OCH$_3$, $R^5$=SCH$_3$, and $R^6$=H; $R^1$=OCH$_3$, $R^2$=OCH$_3$, $R^3$=OCH$_3$, $R^4$=OCH$_3$, $R^5$=OCH$_3$, and $R^6$=H; $R^1$=OCH$_3$, $R^2$=SCH$_3$, $R^3$=OCH$_3$, $R^4$=SCH$_3$, $R^5$=OCH$_3$, and $R^6$=H; $R^1$=Br, $R^2$=OCH$_3$, $R^3$=OCH$_3$, $R^4$=SCH$_3$, $R^5$=OCH$_3$, and $R^6$=H; $R^1$=Br, $R^2$=SCH$_3$, $R^3$=OCH$_3$, $R^4$=SCH$_3$, $R^5$=OCH$_3$, and $R^6$=H; $R^1$=Br, $R^2$=OCH$_3$, $R^3$=Br, $R^4$=SCH$_3$, $R^5$=OCH$_3$, and $R^6$=H; $R^1$=Br, $R^2$=SCH$_3$, $R^3$=Br, $R^4$=SCH$_3$, $R^5$=OCH$_3$, and $R^6$=H; $R^1$=OCH$_3$, $R^2$SCH$_3$, $R^3$=OCH$_3$, $R^4$=OCH$_3$, $R^5$=OCH$_3$, and $R^6$=H; $R^1$=Br, $R^2$=SCH$_3$, $R^3$=OCH$_3$, $R^4$=OCH$_3$, $R^5$=OCH$_3$, and $R^6$=H; $R^1$=Br, $R^2$=SCH$_3$, $R^3$=Br, $R^4$=OCH$_3$, $R^5$=OCH$_3$, and $R^6$=H; $R^1$=OCH$_3$, $R^2$=SCH$_3$, $R^3$=OCH$_3$, $R^4$=OCH$_3$, $R^5$=NO$_2$, and $R^6$=H; $R^1$=Br, $R^2$=SCH$_3$, $R^3$=OCH$_3$, $R^4$=OCH$_3$, $R^5$=NO$_2$, and $R^6$=H; $R^1$=Br, $R^2$=SCH$_3$, $R^3$=Br, $R^4$=OCH$_3$, $R^5$=NO$_2$, and $R^6$=H; $R^1$=OCH$_3$, $R^2$=SCH$_3$, $R^3$=OCH$_3$, $R^4$=OCH$_3$, $R^5$=NH$_2$, and $R^6$=H; $R^1$=Br, $R^2$=SCH$_3$, $R^3$=OCH$_3$, $R^4$=OCH$_3$, $R^5$=NH$_2$, $R^6$=H; $R^1$=Br, $R^2$=SCH$_3$, $R^3$=Br, $R^4$=OCH$_3$, $R^5$=NH$_2$, and $R^6$=H; $R^1$=OCH$_3$, $R^2$=SCH$_3$, $R^3$=OCH$_3$, $R^4$=OCH$_3$, $R^5$=NHC(O)CH(NH$_2$)CH$_2$OH, and $R^6$=H; $R^1$=Br, $R^2$=SCH$_3$, $R^3$=OCH$_3$, $R^4$=OCH$_3$, $R^5$=NHC(O)CH(NH$_2$)CH$_2$OH, and $R^6$=H; or $R^1$=Br, $R^2$=SCH$_3$, $R^3$=Br, $R^4$=OCH$_3$, $R^5$=NHC(O)CH(NH$_2$)CH$_2$OH, and $R^6$=H.

3. A method of treating cancer comprising the step of administering a microtubule-interfering agent comprising a compound of claim 1 to a subject in need thereof.

4. The compounds according to claim 2, wherein the pharmaceutically acceptable salts comprise chlorides, bromides, phosphates, hydrogen sulfates (VI), sulfates (VI), acetates, citrates, tartrates, and lactates.

5. A 4,5-diphenyl-1,3-oxazole derivative of the general formula 2, (2)

wherein $R^1$=Br, $R^2$=OCH$_3$, $R^3$=OCH$_3$, $R^4$=OCH$_3$, $R^5$=SCH$_3$, and R6=H.

6. A pharmaceutically acceptable salt of a 4,5-diphenyl-1,3-oxazole derivative of the general formula 2, (2)

wherein $R^1$=Br, $R^2$=OCH$_3$, $R^3$=OCH$_3$, $R^4$=OCH$_3$, $R^5$=SCH$_3$, and R6=H.

7. A method of treating cancer comprising the step of administering a microtubule-interfering agent comprising a compound of claim 5 to a subject in need thereof.

8. The pharmaceutically acceptable salt of claim 6, comprising a chloride, a bromide, a phosphate, a hydrogen sulfate (VI), a sulfate (VI), an acetate, a citrate, a tartrate, or a lactate.

* * * * *